US008883738B2

(12) United States Patent
Matzke et al.

(10) Patent No.: US 8,883,738 B2
(45) Date of Patent: Nov. 11, 2014

(54) USE OF A PEPTIDE FRAGMENT OF CD44V6 IN THE TREATMENT OF OPHTHALMIC DISEASES

(71) Applicant: Karlsruher Institut für Technologie, Karlsruhe (DE)

(72) Inventors: Alexandra Matzke, Dettenheim (DE); Helmut Ponta, Graben-Neudorf (DE); Véronique Orian-Rousseau, Rittershofen (FR); Martina Tremmel, Weinheim (DE)

(73) Assignee: Karlsruher Insitut für Technologie, Karlsruhe (DE)

( * ) Notice: Subject to any disclaimer, the term of this patent is extended or adjusted under 35 U.S.C. 154(b) by 34 days.

(21) Appl. No.: 13/713,594

(22) Filed: Dec. 13, 2012

(65) Prior Publication Data

US 2013/0109632 A1 May 2, 2013

Related U.S. Application Data

(62) Division of application No. 13/378,574, filed as application No. PCT/EP2010/003523 on Jun. 11, 2010, now abandoned.

(30) Foreign Application Priority Data

Jun. 24, 2009 (EP) ..................................... 09008272

(51) Int. Cl.
*A61P 27/02* (2006.01)
*A61P 9/10* (2006.01)
*A61K 38/08* (2006.01)
*A61K 38/12* (2006.01)
*A61K 38/17* (2006.01)

(52) U.S. Cl.
CPC ............... *A61K 38/08* (2013.01); *A61K 38/177* (2013.01)
USPC ........... 514/20.8; 514/8.1; 514/9.5; 514/13.3; 514/19.1; 514/21.1; 514/21.8; 530/330

(58) Field of Classification Search
None
See application file for complete search history.

(56) References Cited

U.S. PATENT DOCUMENTS 5,916,561 A 6/1999 Adolf et al.

FOREIGN PATENT DOCUMENTS

EP 1 647 556 A1 4/2006
WO WO 2009/023411 A1 2/2009

OTHER PUBLICATIONS

Pieramici et al (2008. Eye. 22: 1330-1336).*
Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Jung, C., et al., "Involvement of CD44v6 in InIB-dependent Listeria Invasion", *Molecular Microbiology*, May 7, 2009, vol. 72(5), pp. 1196-1207.
Schlingemann, R.O., et al., "Treatment of retinal diseases with VEGF antagonists", *J. Verhaagen et al. (Eds.), Progress in Brain Research*, 2009, vol. 175, pp. 253-267.
Cao, Gaoyuan et al., "Involvement of Endothelial CD44 during in Vivo Angiogenesis," American Journal of Pathology, vol. 169, No. 1, Jul. 2006, pp. 325-336.
Singerman, L J, et al., "Pegaptanib Sodium for Neovascular Age-Related Macular Degeneration: Third-Year Safety Results of the VEGF Inhibition Study in Ocular Neovascularisation (VISION) trial," Br J Ophthalmol, 2008, vol. 92, pp. 1606-1611.
Tremmel, Martina et al., "A CD44v6 Peptide Reveals a Role of CD44 in VEGFR-2 Signaling and Angiogenesis," Blood, www.bloodjournal.org, Sep. 2009, pp. 1-38.
Wells, John A., et al., "Levels of vascular endothelial growth factor a4re elevated in he vitreous of patients with subretinal neovascularisation" British Journal of Ophthalmology (1996), vol. 80, pp. 363-366.
Ambati, Jayakrishna et al., "Age-related macular degeneration: Etiology, Pathogenesis, and Therapeutic Strategies" Survey of Ophthalmology (2003), vol. 48, No. 3, pp. 257-293.
Aiello, Lloyd Paul et al., "Vascular endothelial growth factor in ocular fluid of patients with diabetic retinopathy and other retinal disorders" The New England Journal of Medicine (1994), pages.

* cited by examiner

*Primary Examiner* — Zachary Howard
(74) *Attorney, Agent, or Firm* — McDonnell Boehnen Hulbert & Berghoff LLP

(57) ABSTRACT

The present invention relates to the use of peptide compounds for the prevention and/or treatment of ophthalmic diseases. In particular, the present invention relates to a peptide compound comprising an amino acid sequence displayed by amino acids 7 to 11 of SEQ ID NO: 2 (KEQWFGNRWH-EGYR) or of SEQ ID NO: 1 (KEKWFENEWQGKNP), or a functionally active derivative thereof, or a pharmaceutically acceptable salt thereof, for use in the prevention and/or treatmend of an ophthalmic disease in an individual. While SEQ ID NO: 2 is a part of the human CD44v6, SEQ ID NO: 1 is a part of the rat CD44v6.

6 Claims, 8 Drawing Sheets

USE OF A PEPTIDE FRAGMENT OF CD44V6 IN THE TREATMENT OF OPHTHALMIC DISEASES

CROSS REFERENCE TO RELATED APPLICATIONS

Figure 1:
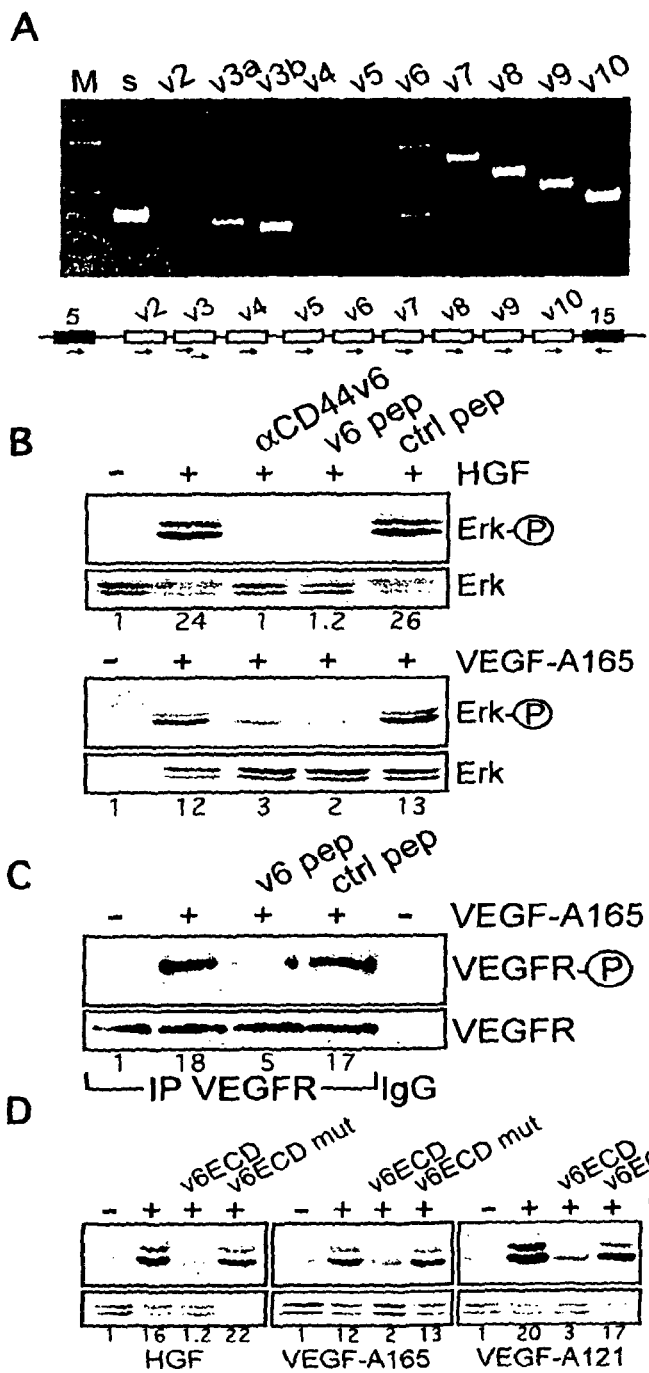

The present application is a divisional of U.S. patent application Ser. No. 13/378,574, filed Jan. 23, 2012, which in turn is a 35 U.S.C. 371 National Application of PCT/EP2010/003523, filed Jun. 11, 2010, which claims priority to European Patent Application No. 09 008 272.8, filed Jun. 24, 2009.

The present invention relates to the use of peptide compounds for the prevention and/or treatment of ophthalmic diseases.

Angiogenesis is a complex process that leads to the formation of new blood vessels from existing ones. During embryogenesis, angiogenesis complements vasculogenesis, the production of new blood vessels from hematopoietic precursors. In contrast, in the adult organism, angiogenesis takes place under normal conditions during the female reproductive cycle or under pathological conditions such as in tumor growth and wound healing. Secretion of angiogenic factors from the tumor mass induces the formation of blood vessels, which feed cancer cells with oxygen and nutrients. These vessels will eventually be used as a route for the spreading of metastases.

Several angiogenic factors have been described including VEGF (vascular endothelial growth factor), FGF, TGF-α, TGF-β, HGF, TNF, angiogenin, IL-8 and the angiopoietins. The most prominent angiogenic factor is VEGF-A, a member of the VEGF family of growth factors including PlGF (Placental Growth Factor), VEGF-B, C, D and E. VEGFs bind to three related members of the VEGFR family, VEGFR-1, 2 and 3. The importance of VEGFs and their receptors is demonstrated by the phenotypes of the respective knockout mice. Indeed, VEGF-A and VEGFR-2 knockout mice show a failure in vasculature formation and die during embryogenesis whereas VEGFR-1-deficient mice die of an overgrowth of blood vessels. Fighting angiogenesis has become a very attractive aim for cancer therapy. Indeed, targeting angiogenesis rather than directly addressing the tumor cells has the advantage that the same reagents can be applied to many different types of tumors.

In addition, due to the low turnover rate of ECs (endothelial cells), they are less susceptible to become resistant to chemotherapy. Several anti-VEGF treatment regimens already exist that can be combined with chemotherapy or radiotherapy. These treatments make use of VEGF inhibitors such as antibodies against VEGF (bevacizumab), several small molecules inhibiting VEGFR-2 signaling as well as soluble VEGF receptors that compete with the endogenous receptor for binding to VEGF. However, since all these treatments have a relatively modest benefit for most cancer patients, there is still plenty of room for improvement.

HGF is another potent angiogenic factor: the expression of HGF and its receptor c-Met correlates with tumor vascularization, the production of VEGF in a variety of cells and tissues is induced by HGF and HGF can potentiate the activity of VEGF. Furthermore HGF leads to mobilization of endothelial progenitor cells and the expression of a soluble c-Met receptor (decoy Met) impairs tumor angiogenesis. The CD44 family of cell adhesion proteins comprises a variety of isoforms that differ in the extracellular domain. In this region, 10 variant exons can be either completely excluded (the smallest isoform CD44s) or included by alternative splicing in various combinations (variant isoforms, CD44v). The expression of these CD44v isoforms is often upregulated in cancer. CD44 isoforms containing the variant exon v6 have been shown to be metastatic determinants. The role of CD44v6 in metastasis results most probably from its cooperation with the RTK c-Met. In many carcinoma and primary cells, the activation and signaling from the c-Met receptor is dependent on CD44v6 isoforms and can be blocked by CD44v6 specific antibodies, by CD44v6 siRNA and, most interestingly, by CD44 exon v6 specific peptides. These isoforms play a dual role for c-Met dependent signaling. Their extracellular part is required for c-Met activation, whereas the cytoplasmic domain of CD44 recruits ERM proteins (ezrin, radixin, moesin) that bind the cytoskeleton and promote activation of Ras by its guanidine exchange factor (GEF) SOS.

A collaboration between CD44 and c-Met was also confirmed in vivo since c-Met is haploinsufficient in the context of CD44 null mice. Composite cd44−/−, met+/− mice show severe breathing defects and die at birth. In these mice, synaptic transmission in the respiratory rhythm-generating network is impaired in the brain. In addition, Schwann cell differentiation in the phrenic nerve is altered.

CD44 proteins have already been shown to be relevant for angiogenesis: bFGF and VEGF, two important angiogenic factors up regulate CD44 on ECs in vivo and targeting of CD44 by specific antibodies leads to EC killing. CD44 specific antibodies repress EC proliferation and capillary formation in fibrin matrix. The proliferation of ECs and their adhesion to hyaluronan, a component of the ECM, is dependent on CD44. CD44 together with bFGF is involved in tubule formation of ECs in collagen gels. Finally CD44v3 was detected in ECs and v3 specific antibodies blocked chemotaxis of these cells. Interestingly, low molecular weight hyaluronan, a degradation product of matrix hyaluronan released upon tissue injury and inflammation, stimulates EC proliferation by binding to CD44. This leads to activation of the MAP kinase pathway and subsequent induction of early response genes.

In addition to its role in the activation of VEGFR-2, CD44v6 is also necessary for intracellular signal transduction. For the activation of the MAPK pathway the CD44v6 cytoplasmic domain appears to recruit ERM proteins and the cytoskeleton in order to allow Ras activation by its GEF SOS similarly to what has been shown for c-Met in epithelial cells. This is particularly interesting since the MAPK pathway plays a crucial role in angiogenesis for proliferation, survival and migration of ECs. Furthermore Mek1 knockout mice are embryonic lethal and die from a placental defect caused by impaired angiogenesis. The MAPK pathway has been shown to induce EC survival and sprouting by inhibiting Rho. VEGF has been described as a heparin binding growth factor and has been shown to bind to CD44 exon v3 containing isoforms that carry HS. VEGF-A121 is a less potent EC mitogen and has a 10-100 fold lower biological activity than VEGF-A165. Neuropilin 1 (NRP1), a HS modified protein that can bind VEGF-A165 but not VEGF-A121, seems a good candidate to provide HS moieties.

Numerous experimental and clinical studies have show the important role of VEGF in most neovascular and exudative ophthamlic diseases. Anti-VEGF therapies have shown promising results in a number of prospective controlled clinical trials. Additionally, in the treatment of neovascular age-related macular degeneration (AMD) intravitreal anti-VEGF therapy has shown to stabilize vision in most patients and to improve vision in a significant number of patients. Additionally, it is well known that the expression of retinal VEGFR is increased in patients suffering from diabetic retinopathy.

Therefore, the technical problem underlying the present invention is to provide a novel medicament that can be used for the prevention and/or treatment of ophthalmic diseases.

The solution to the above technical problem is achieved by the embodiments characterized in the claims.

In particular, the present invention relates to a peptide compound comprising an amino acid sequence displayed by amino acids 7 to 11 of SEQ ID NO: 2 (KEQWFGNRWH-EGYR) or of SEQ ID NO: 1 (KEKWFENEWQGKNP), or a functionally active derivative thereof, or a pharmaceutically acceptable salt thereof, for use in the prevention and/or treatment of an ophthalmic disease in an individual. While SEQ ID NO: 2 is a part of the human CD44v6, SEQ ID NO: 1 is a part of the rat CD44v6.

In another aspect, the present invention relates to a peptide compound comprising an amino acid sequence displayed by SEQ ID NO: 2 or SEQ ID NO: 1, or a functionally active derivative thereof, or a pharmaceutically acceptable salt thereof, for use in the manufacture of a medicament for the prevention and/or treatment of an ophthalmic disease in an individual.

In a preferred embodiment, the peptide compound of the present invention is a peptide consisting of amino acids 7 to 11 of SEQ ID NO: 2 or of SEQ ID NO: 1.

In another preferred embodiment of the present invention, the peptide compound of the present invention is a peptide consisting of SEQ ID NO: 2 or SEQ ID NO: 1.

The peptide compound of the present invention may be any peptide compound described in European patent application EP 1 647 556.

In a preferred embodiment, the peptide compound of the present invention comprises or consists of a fragment of SEQ ID NO: 2 or of SEQ ID NO: 1, said fragment having the activity of inhibiting the complex formation between CD44 and VEGFR-2.

For example the peptide compound of the present invention is selected from the group consisting of
(a) peptides comprising or consisting of the amino acid sequence as shown in SEQ ID NO: 2 or SEQ ID NO: 1;
(b) peptides consisting of a fragment of SEQ ID NO: 2 or of SEQ ID NO: 1, and having the activity of inhibiting the complex formation between CD44 and VEGFR-2;
(c) heterologous fusion peptides comprising or consisting of a peptide according to (a) or (b) fused to a heterologous amino acid sequence; and
(d) derivatives of a peptide according to (a), (b) or (c) having the activity of inhibiting the complex formation between CD44 and VEGFR-2.

In a preferred embodiment of the present invention, the peptide compound of the present invention is selected from the group consisting of
(a) peptides comprising or consisting of the amino acid sequence as shown in SEQ ID NO: 2 or SEQ ID NO: 1,
(b) peptides comprising or consisting of any one of the following amino acid sequences:
amino acids 2 to 14 of SEQ ID NO: 2 or 1,
amino acids 2 to 13 of SEQ ID NO: 2 or 1,
amino acids 2 to 12 of SEQ ID NO: 2 or 1,
amino acids 2 to 11 of SEQ ID NO: 2 or 1,
amino acids 3 to 14 of SEQ ID NO: 2 or 1,
amino acids 3 to 13 of SEQ ID NO: 2 or 1,
amino acids 3 to 12 of SEQ ID NO: 2 or 1,
amino acids 3 to 11 of SEQ ID NO: 2 or 1,
amino acids 4 to 14 of SEQ ID NO: 2 or 1,
amino acids 4 to 13 of SEQ ID NO: 2 or 1,
amino acids 4 to 12 of SEQ ID NO: 2 or 1,
amino acids 4 to 11 of SEQ ID NO: 2 or 1,
amino acids 5 to 14 of SEQ ID NO: 2 or 1,
amino acids 5 to 13 of SEQ ID NO: 2 or 1,
amino acids 5 to 12 of SEQ ID NO: 2 or 1,
amino acids 5 to 11 of SEQ ID NO: 2 or 1,
amino acids 6 to 14 of SEQ ID NO: 2 or 1,
amino acids 6 to 13 of SEQ ID NO: 2 or 1,
amino acids 6 to 12 of SEQ ID NO: 2 or 1,
amino acids 6 to 11 of SEQ ID NO: 2 or 1,
amino acids 7 to 14 of SEQ ID NO: 2 or 1,
amino acids 7 to 13 of SEQ ID NO: 2 or 1,
amino acids 7 to 12 of SEQ ID NO: 2 or 1,
amino acids 7 to 11 of SEQ ID NO: 2 or 1, and
(c) heterologous fusion peptides comprising (a) or (b) fused to a heterologous amino acid sequence.

The peptide compound of the present invention may comprise amino acid sequences derived from other proteins. Therefore, in a preferred embodiment, the peptide compound of the present invention comprises fusion peptides comprising one of the above amino acid sequences fused to a another, preferably heterologous, amino acid sequence. The heterologous amino acid sequence may comprise or consist of 1, 2, 3, 4 or more amino acids. The heterologous amino acid sequence may for example comprise or consist of at least 5 or at least 10 or at least 20 heterologous amino acids. The heterologous amino acid sequences may be fused to the N- and/or C-terminus of the peptide compound of the present invention.

In a further embodiment of the present invention, the peptide compound of the present invention is a derivative of the peptides described above. The term "derivative" as used herein comprises functionally active derivatives, variants and chemical derivatives of the peptide compound and includes post-translational modifications, e.g. glycosylation patterns that differ from the wild-type.

The term "functionally active derivative" as used herein relates to derivatives which contain deletions, additions and/or substitutions of amino acids, the presence, absence or substitution of which does not have a substantial influence on the activity of the peptide compound, e.g. conservative amino acid substitutions, i.e. substitution of an amino acid by an amino acid having similar chemical properties.

A "variant" of a peptide is meant to refer to a molecule substantially similar to either the entire peptide, or a fragment thereof having essentially the same function. A variant of a first peptide may be a second peptide which has 1 to 5, preferably 1 to 4, more preferably 1 to 3, more preferably 1 or 2 amino acid substitutions, additions and/or deletions with respect to said first peptide. For example, variants of SEQ ID NO: 2 may have 1 to 5 amino acid substitutions with respect to SEQ ID NO: 2, as long as the activity of inhibiting the complex formation between CD44 and VEGFR-2 leading to the phosphorylation and internalization of c-Met, as well as to phosphorylation of Erk, is substantially the same as that of the peptide consisting of the amino acid sequence as shown in SEQ ID NO: 2.

A molecule is a "chemical derivative" of a first peptide when it contains additional chemical moieties not present in the first peptide. Such moieties may improve for example the molecule's solubility, absorption, or biological half-life. The moieties may alternatively for example decrease the toxicity of the molecule, or eliminate or attenuate any undesirable side effect of the molecule.

Generally, the derivative has at least 75%, preferably at least 100% of the activity of inhibiting the complex formation between CD44 and VEGFR-2 of the peptide compound from which it is derived.

The term "fragment" of a given peptide as used herein is meant to refer to any peptide subset of said peptide. Generally, a fragment comprises at least 2 contiguous amino acids of the sequence of said peptide. Preferably, the fragment comprises at least 4, more preferably at least 5, more preferably at least 6, more preferably at least 8, even more preferably at least 10 contiguous amino acids of said peptide.

Methods for determining the activity of inhibiting the complex formation between CD44 and VEGFR-2 are well known in the art. The peptide compound of the invention has the activity of inhibiting the complex formation between CD44 and VEGFR-2. The inhibitory activity results in a reduction of downstream VEGFR-2 activation. Preferably, downstream VEGFR-2 activation is reduced by at least 30%, more preferably by at least 50% and even more preferably by at least 70% with respect to the downstream VEGFR-2 activation in the presence of a control peptide. For example the activity can be determined in cell culture or in vivo.

The term "peptide compound" as used herein denotes a compound comprising at lease one peptide. In one embodiment of the present application the "peptide compound" consists of a peptide. The term "peptide compound" includes compounds comprising a peptide and a chemical moiety which is not an amino acid.

The term "peptide" as used herein refers to any compound comprising two or more amino acids joined to each other by peptide bonds or modified peptide bonds, i.e. peptide isosteres. "Peptide" refers to both short chains and to longer chains, generally referred to as polypeptides. Peptides may contain amino acids other than the 20 gene-encoded amino acids. Peptides include amino acid sequences modified either by natural processes, such as post-translational processing, or by chemical modification techniques which are well known in the art. Modifications can occur anywhere in a peptide, including the peptide backbone, the amino acid side-chains and the amino or carboxyl termini. The same type of modification may be present in the same or varying degrees at several sites in a given peptide. Also, a given peptide may contain many types of modifications.

Peptides may be branched and they may be cyclic, with or without branching. Cyclic, branched and branched cyclic peptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, ubiquitination and sumoylation.

The term "peptide compound" may as a preferred embodiment include salts, preferably pharmaceutically acceptable salts of the peptides described herein. Salts encompassed within the term "pharmaceutically acceptable salts" refer to non-toxic salts of the peptide compounds of this invention. Representative salts and esters include the following: acetate, ascorbate, benzenesulfonate, benzoate, bicarbonate, bisulfate, bitartrate, borate, caamsylate, carbonate, citrate, dihydrochloride, methanesulfonate, ethanesulfonate, p-toluenesulfonate, cyclohexylsulfamate, quinate, edetate, edisylate, estolate, esylate, fumarate, gluconate, glutamate, glycerophophates, hydrobromide, hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate, and valerate. Other salts include Ca, Li, Mg, Na, and K salts; salts of amino acids such as lysine or arginine; guanidine, diethanolamine or choline; ammonium, substituted ammonium salts or aluminum salts. The salts are prepared by conventional methods.

The peptide of the invention has a length of at least 2 amino acids. Preferably, the length of the peptide is at least 4, more preferably at least 5, more preferably at least 6, more preferably at least 8, most preferably at least 10 amino acids. The maximum length is not particularly limited. It is preferred, however, that the peptide has a length of from about 6 to about 30 amino acids, preferably of from about 8 to about 25 amino acids, more preferably of from about 10 to about 20 amino acids, most preferably of from about 10 to about 15 amino acids. Larger peptides may be employed, for example when fusion peptides with heterologous amino acid sequences are prepared.

It is preferred that the peptide of the present invention is an isolated peptide.

It is also preferred that the peptide of the present invention is in a pure state. Preferably, the peptide is 80% pure, preferably 90% pure, more preferably 95% pure, even more preferably 99% pure and particularly preferred is a pharmaceutically pure state that is greater than 99.9% pure with respect to contaminating macromolecules, particularly other peptides. It is preferred that the peptide is free of infectious and pyrogenic agents.

Preferably, a purified peptide is substantially free of other peptides. When used in this context, the term "pure" does not exclude the presence of the same peptide in alternative physical forms, such as dimers.

The peptides of the present invention may be prepared by chemical synthesis or by recombinant expression in host cells. The preparation by chemical synthesis is preferred. As protein products, compounds of SEQ ID NO: 2 or 1 or other peptides of the present invention are amenable to production by the technique of solution- or solid-phase peptide synthesis. The synthetic peptide synthesis approach generally entails the use of automated synthesizers and appropriate resins as solid phase, to which is attached the C-terminal amino acid of the desired peptide. Extension of the peptide in the N-terminal direction is then achieved by successively coupling a suitably protected form of the next desired amino acid, using either FMOC- or BOC-based chemical protocols typically, until synthesis is complete. Protecting groups are then cleaved from the peptide, usually simultaneously with cleavage of peptide from the resin, and the peptide is then isolated and purified using conventional techniques, such as by reversed phase HPLC using acetonitrile as solvent and trifluoroacetic acid as ion-pairing agent. Such procedures are generally described in numerous publications.

The peptide compound of the present invention may be a chemically derived structure, diverted from the peptide sequences described herein, or a pharmaceutically acceptable salt and/or physiologically functional derivative thereof. The chemically derived structure can be a cyclopeptide or a pharmaceutically acceptable salt and/or physiologically functional derivative thereof. The invention further includes the use of a substance metabolized to a peptide compound of the invention.

The individual according to the present invention may be any individual which is susceptible to an ophthalmic disease, like a vertebrate. In a preferred embodiment the individual is a mammal, like for example a mouse, a rat, a human, a rabbit, a pig a cattle, or a horse, and most preferably a rat or a human.

In a preferred embodiment, the peptide compound comprises an amino acid sequence displayed by at least amino acids 7 to 11 of SEQ ID NO: 1, or a functionally active derivative thereof, or a pharmaceutically acceptable salt thereof, for use in the prevention and/or treatment of an ophthalmic disease in a rat. In another preferred embodiment, the peptide compound comprises an amino acid sequence displayed by at least amino acids 7 to 11 of SEQ ID NO: 2, or a functionally active derivative thereof, or a pharmaceutically acceptable salt thereof, for use in the prevention and/or treatment of an ophthalmic disease in a human.

In a preferred embodiment of the present invention, the ophthalmic disease is associated with angiogenesis, for example the ophthalmic disease can be associated with overexpression of VEGFR-2. According to the present invention, the ophthalmic disease can be for example caused by the overexpression of VEGFR-2 and/or the ophthalmic disease can be associated with hyperproliferation of endothelial cells.

In another preferred embodiment of the present invention, the ophthalmic disease is selected from the group consisting of macular degeneration, diabetic retinopathy. In a particularly preferred embodiment of the present invention, the ophthalmic disease is macular degeneration or diabetic retinopathy.

In another object of the present invention a method for the treatment of an ophthalmic disease as defined above comprising the step of administering the peptide of the present invention in a suitable amount is provided.

The medicament of the present invention can be formulated as e.g., liquids, suspensions, emulsions, lozenges, cachets, ampoules, suppositories, pessaries, ointments, gels, pastes, sprays, lotions, oils, boluses, electuaries, aerosols, powders, granules, tablets, pills, capsules, injections, solutions, foams, creams, enemas and the like, comprising at least one compound of the present invention alone or in admixture with pharmaceutically acceptable carriers, excipients and/or diluents.

Specific dose levels of the medicament of the present invention for any particular patient will be employed depending upon a variety of factors including the age, body weight, general health, sex, diet, and prior medication, and the severity of the particular disease of the patient, and the activity of specific compounds employed, time of administration, route of administration, rate of excretion, the duration of the treatment, other drugs, compounds, and/or materials used in combination. The appropriate dosage of medicament can vary from patient to patient. Determining the optimal dosage will generally involve balancing of the level of therapeutic benefit against any risk or deleterious side effects of the treatment.

Administration in vivo can be effected in one dose, continuously or intermittently throughout the course of treatment. Methods of determining the most effective means and dosages of administration are well known to those of skill in the art, and will vary with the formulation used for therapy, the purpose of the therapy, the target cell being treated, and the subject being treated. Single or multiple administrations can be carried out with the dose level and pattern being selected by the treating physician.

In general, a suitable systemic dose of the active compound of the medicament of the present invention is in the range of about 0.01 to about 1000 mg per kilogram body weight preferably 0.1 to 500 mg per kilogram body weight and even more preferably 1.0 to 500 mg per kilogram body weight of the subject per day. Where the active ingredient is a salt, an ester, prodrug, or the like, the amount administered is calculated on the basis of the parent compound and so the actual weight to be used is increased proportionately. In case the compound is applied locally, the amount of compound may vary from the above given estimation. However, such an application would aim at reaching local concentrations of the drug ranging from about 0.1 ng/ml to 10 mg/ml, more preferred from 1 ng/ml to 1 mg/ml.

According to the present invention, a specific splice variant of the CD44 cell surface protein family, CD44v6 which has the amino acid sequence displayed in SEQ ID NO: 1 when originating from rat, or the amino acid sequence displayed in SEQ ID NO: 2 when originating from human, has been shown to act as a co-receptor for the receptor tyrosine kinase (RTK) c-Met on epithelial cells. In particular, also on endothelial cells, the activity of c-Met is dependent on CD44v6. Furthermore, another RTK, VEGFR-2, which regulates migratory behavior of endothelial cells, is also regulated by CD44v6. The CD44v6 ectodomain and a small peptide mimicking a specific extracellular motif of CD44v6 or antibodies that block this epitope prevent CD44v6 mediated receptor activation. This indicates that the extracellular part of CD44v6 is required for interaction with c-Met or VEGFR-2. In the cytoplasm signaling by activated c-Met and VEGFR-2 requires association of the CD44 carboxyterminus with ezrin that couples CD44v6 to the cytoskeleton. CD44v6 controls endothelial cell migration, sprouting, tubule formation induced by HGF or VEGFA, and the response to angiogenic factors released by transformed Langerhans islets. In vivo the development of blood vessels from grafted endothelial cell spheroids and angiogenesis in tumors is impaired by CD44v6 blocking reagents suggesting that the co-receptor function of CD44v6 for c-Met and VEGFR-2 is a promising target to block angiogenesis in pathological conditions.

Therefore, the CD44v6 peptide can advantageously used as an angiogenic inhibitor, for example in the prevention and/or treatment of ophthalmic diseases which are associated with overexpression of VEGFR-2. The advantage of using a CD44v6 peptide for such a therapy could be several fold. First, according to their small size (14mer or even 5mer), they can be readily produced, they are unlikely to induce an immune response, and they can be easily delivered to their target sites. In addition, they can block several RTKs, are efficient against angiogenesis and metastasis and might be effective also in the therapy of several types of tumors.

The figures show:

FIG. 1: Co-receptor function of CD44v6 in ECs

A: CD44 variant exon specific RT-PCR analysis in HUVEC (see experimental procedures). s refers to the use of two primers in the CD44 constant exons 5 and 15 (black boxes in the schematic drawing of the relevant parts of the CD44 gene), the other lanes refer to PCRs performed with the forward primers in variant exons and the reverse primer in exon 15. M refers to a DNA ladder.

B: Signal transduction induced by HGF or VEGF-A165 in untreated HUVEC or HUVEC treated with a CD44v6 specific antibody (aCD44v6) or the human v6 specific 14mer peptide or a control peptide (see experimental procedures). Activation of Erk was measured as described in experimental procedures.

C: Activation of VEGFR-2 by VEGF-A165 in HUVEC was determined after immunoprecipitation of VEGFR-2 and Western Blotting with the phospho-specific VEGFR-2 antibody (see experimental procedures). IgG indicates a control precipitation. Treatment with VEGF-A165 and with the peptides was performed as described in experimental procedures.

D: Induction of signaling in HUVEC by the ligands as indicated in the presence of the CD44v6ECD (CD44v6 ectodomain) or a mutated version as indicated. Treatments were done as described in experimental procedures.

The numbers indicate the fold induction as calculated by the computer program Image J.

Figure 2:
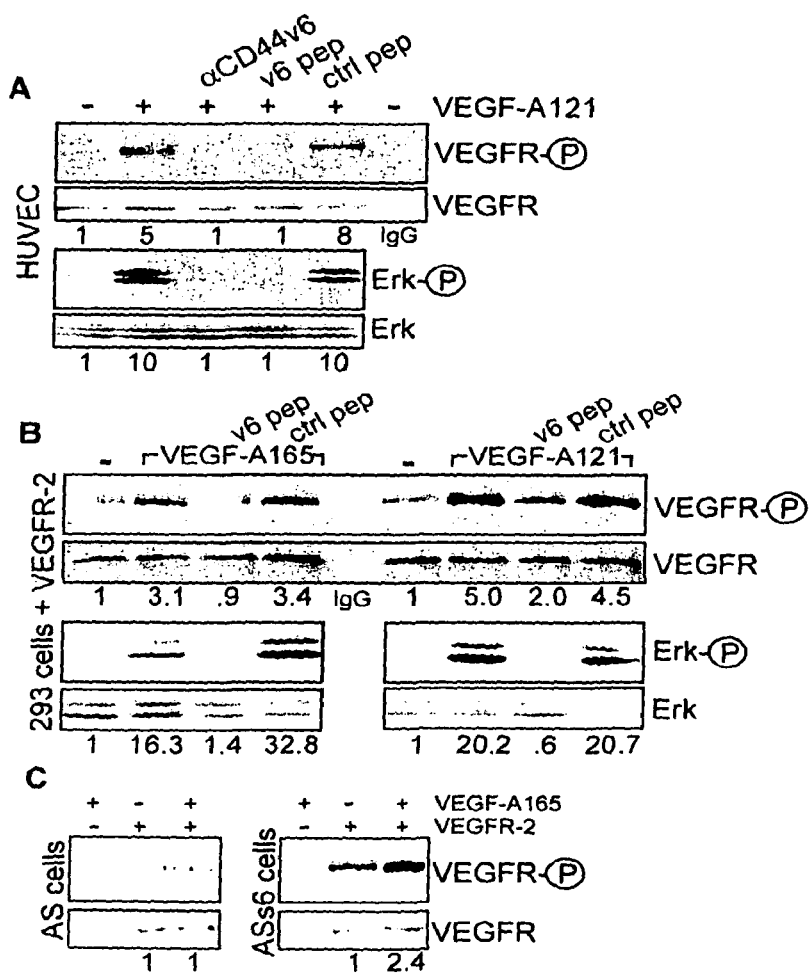

FIG. 2: The co-receptor function of CD44v6 is independent of heparin sulfation

A: HUVECs were induced by VEGF-A121 in the presence of the CD44v6 specific antibody and peptide as indicated. The activation of VEGFR-2 (as in FIG. 1C) and Erk was determined. The IgG lane corresponds to an immunoprecipitation with the IgG control antibody.

B: HEK293 cells were transiently transfected with a VEGFR-2 expression construct (experimental procedures). They were then treated with VEGF and peptides as indicated and the activation of VEGFR-2 (as in FIG. 1C) or signaling to Erk was measured.

C: BSp73AS cells (AS) or BSp73ASs6 cells were transiently transfected with a VEGFR-2 expression construct and activated with VEGF-A165 where indicated. Activation of VEGFR-2 was determined using the phospho VEGFR-2 specific antibody (Tyr 1175) directly in Western Blotting.

The numbers refer to fold induction.

Figure 3:
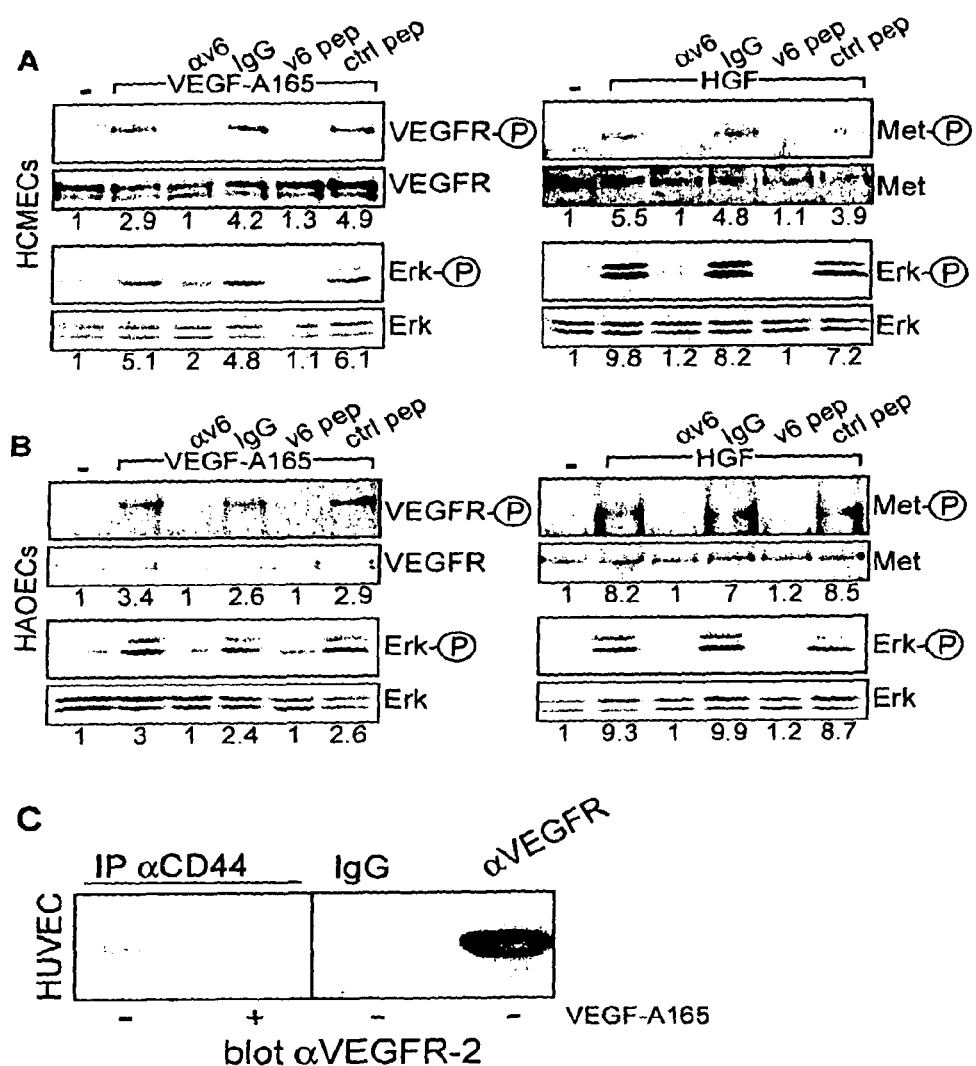

FIG. 3: VEGFR-2 and CD44v6 form a complex

Receptor activation induced by HGF or VEGF-A165 in HCMECs (human cardiac microvascular ECs) (A) and in HAOECs (human aortic ECs) (B) in the presence of a CD44v6 specific antibody (av6), IgG control or the human v6 specific 14mer peptide or a control peptide (Experimental procedures). Activation of Erk was measured as described in experimental procedures.

C: Immunoprecipitation of CD44 from HUVEC treated or not with VEGF-A165 using the CD44 specific antibody IM7 and Western Blotting with the VEGFR-2 antibody. Precipitation with an unrelated IgG antibody or a VEGFR-2 antibody were used as controls.

Figure 4:
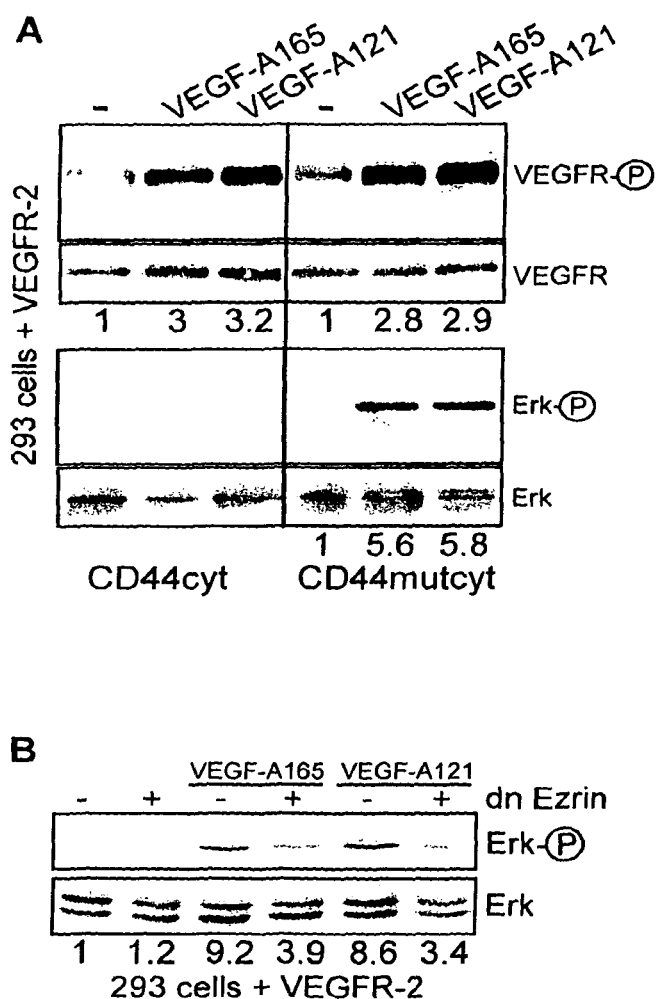

FIG. 4: VEGFR-2 signaling is dependent on ezrin binding to CD44

A: HEK293 cells transiently transfected with a VEGFR-2 expression construct were co-transfected with vectors expressing either the CD44 cytoplasmic domain (CD44cyt) or the CD44 cytoplasmic domain mutated in the Ezrin binding site (CD44mutcyt; experimental procedures). Activation of VEGFR-2 upon induction with VEGF (as described in FIG. 2C) and signaling to Erk were determined.

B: HEK293 cells transiently transfected with a VEGFR-2 expression construct were co-transfected with vectors expressing dominant negative ezrin (dn Ezrin) as indicated and signaling to Erk upon VEGF treatment was determined.

The numbers indicate fold induction.

Figure 5:
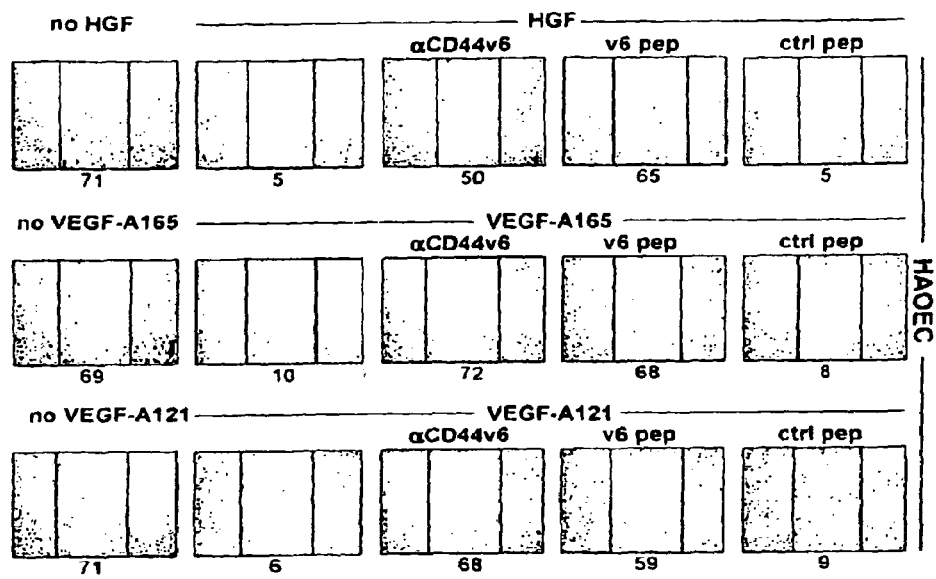
Figure 5:
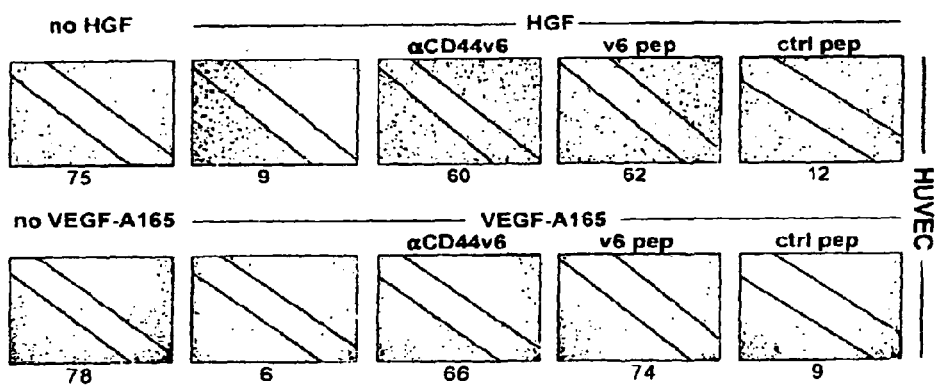

FIG. 5: Migration of ECs requires CD44v6

A scratch wound closing assay was performed with confluent HUVEC or HAOEC treated either with HGF, VEGF-A165 or VEGF-A121 and the peptides or antibodies as indicated (see experimental procedures). The numbers indicate the percentage of free area in the scratch area after 24 h of treatment quantified by using the NIH Image J analysis program.

Figure 6:
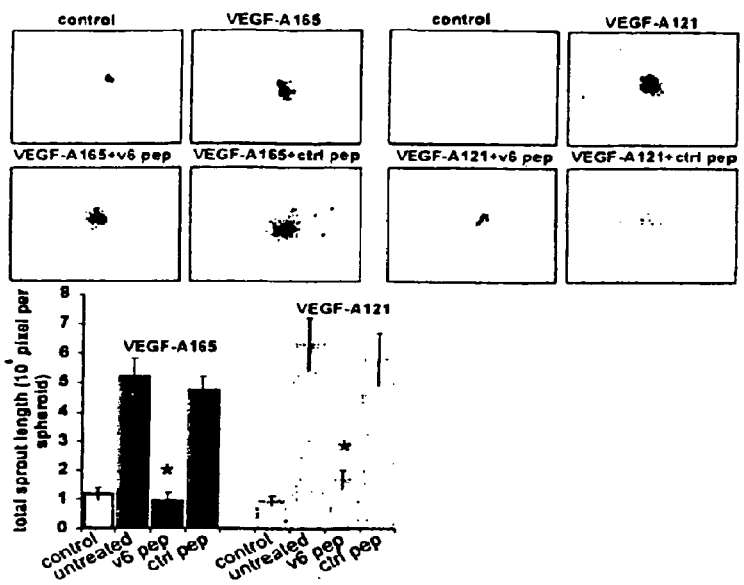
Figure 6:
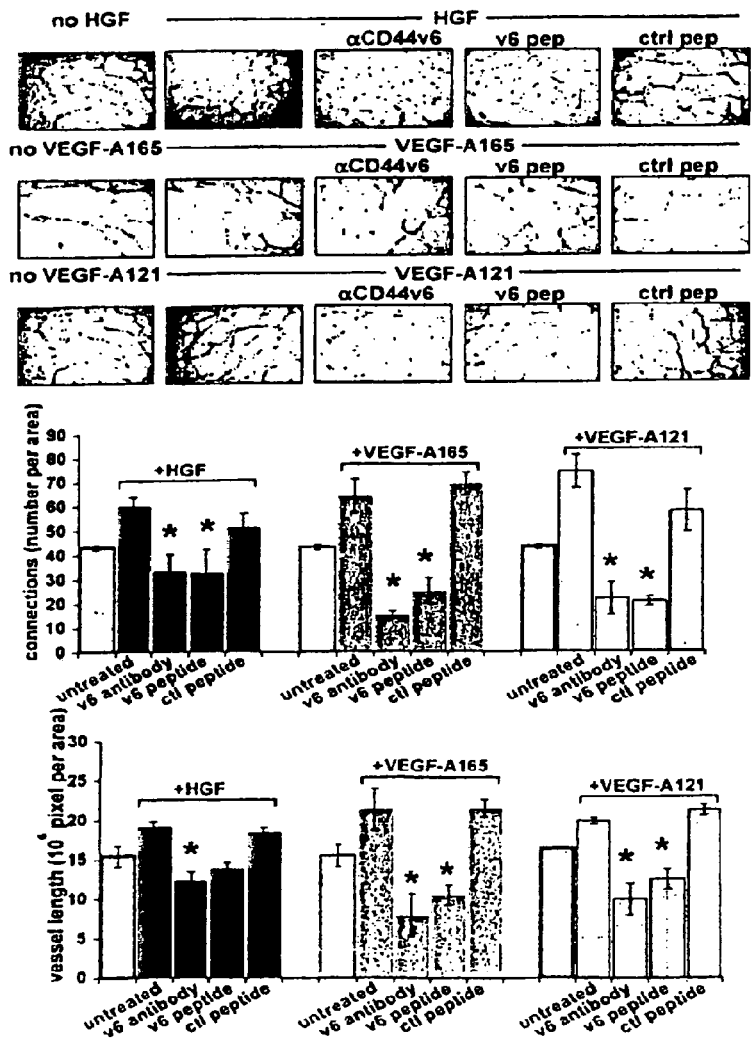

FIG. 6: Sprouting of endothelial spheroids and tube formation of HUVEC depend on CD44v6

A: Spheroids of HUVECs (see experimental procedures) were placed in collagen and treated as indicated. Sprouting was examined after 48 h and quantified with the computer program Image J.

B: Vessel formation of HUVECs on top of a Matrigel layer and their quantification was determined as described in experimental procedures.

The asterisk indicates the statistical significance (p-values below 0.05). The standard deviation was calculated from three independent experiments.

Figure 7:
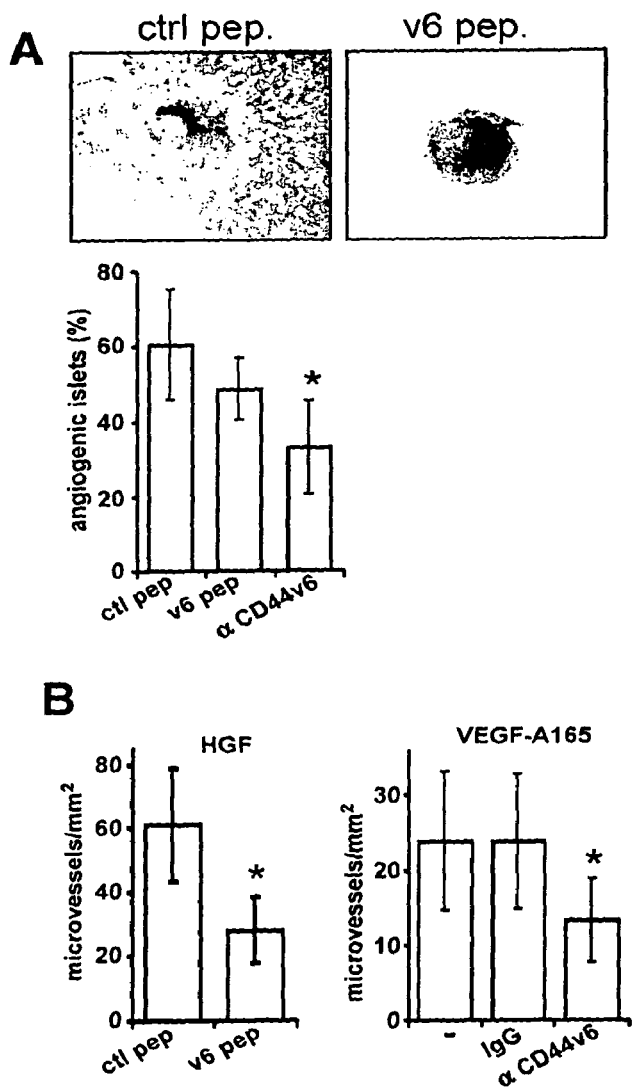

FIG. 7: The angiogenic response of HUVEC to Langerhans islets and the formation of a vasculature in vivo requires CD44v6

A: HUVECs were incubated with hyperplastic angiogenic Langerhans islets of Rip1Tag2 mice, obtained 8 to 9 weeks after birth in the absence or presence of CD44v6 specific inhibitors. The angiogenic response is shown in the left picture, as compared to a non-angiogenic nodule, right picture. For quantification 60 islets were analyzed.

B: Spheroids of HUVECs in a Matrigel/fibrin matrix were injected subcutaneously into SCID mice together with growth factors (HGF or VEGF-A165) and a peptide or an antibody as indicated (see experimental procedures). The number of microvessels formed in the Matrigel/fibrin plug was determined 21 days after implantation. A minimum of 3 different plugs per condition were analyzed.

Figure 8:
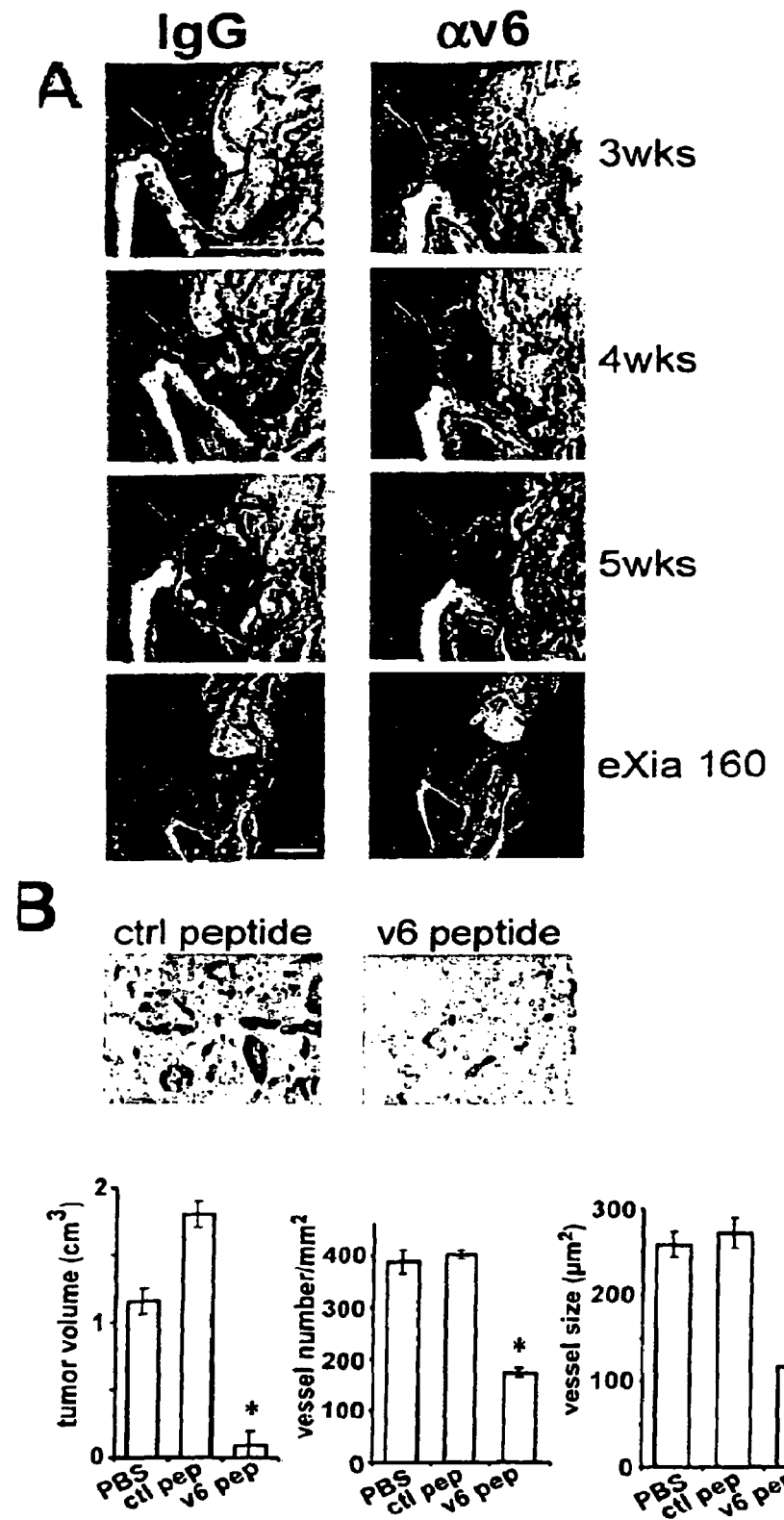

FIG. 8: Tumor-induced angiogenesis is inhibited by a CD44v6 peptide and antibody A: Tumors and tumor vessels visualized in vivo by 3D reconstruction of fpVCT (flat-panel detector Volume Computed Tomography) data sets over time. MDA-MB231 cells were orthotopically implanted into SCID mice (see experimental procedures). One week later the mice were treated with control IgG or a mouse CD44v6 antibody three times per week for four weeks. The pictures show representative tumor bearing animals three, four and five weeks after implantation. For better demonstration of small blood vessels, the blood pool agent eXia 160 was used instead of the conventional contrast agent Isovist 300 for the final scans. The localisation of the tumors is indicated by arrows. Note, that the density of small vessels surrounding and invading the tumor is decreased in mice treated with the CD44v6 antibody in comparison to controls. A quantification of the experiment is shown in Table 1. Scale bars: 10 mm.

B: Human pancreatic cancer cells (L3.6pl) were orthotopically implanted in nude mice (see experimental procedures). One week later the mice were treated with PBS, a control peptide or a mouse specific CD44v6 peptide three times per week for three weeks. The animals were then sacrificed and tumor sections were stained with the endothelial marker CD31. A representative staining is shown. Tumor volume, vessel number and average vessel size (see Methods) from five animals were determined and the results are shown in the graph.

The present invention will now be further illustrated in the following examples without being limited thereto.

EXAMPLES

Experimental Procedures:

Cells and cell culture Human umbilical vein endothelial cells (HUVEC, Provitro GmbH, Berlin, Germany) were grown in Endothelial Cell Growth Medium complemented with the SupplementMix (Provitro GmbH, Berlin, Germany). The Human aortic endothelial cells (HAOEC, Promocell, Heidelberg, Germany) and human cardiac microvascular endothelial cells (HCMEC, Promocell, Heidelberg, Germany) were grown in Endothelial Cell Growth Medium MV (Promocell, Heidelberg) completed with the supplements according to the manufacturer's instructions. All ECs were not passaged more than 9 times. The HEK293 cells (American Tissue Culture Collection, ATCC, Wesel, Germany) and the estrogen-independent human breast cancer cell line MDA-MB231 (American Type Culture Collection, Rockville, Md.) were grown in DMEM (Invitrogen, Karlsruhe, Germany) supplemented with 10% FCS (PAA Laboratories, Coelbe, Germany). The rat pancreatic carcinoma cell line BSp73AS and its transfectant (Bsp73ASs6) were grown in RMPI (Invitrogen, Karlsruhe, Germany) plus 10% FCS. The human pancreatic cancer cell line L3.6pl, kindly provided by C. Bruns, University of Munich, Germany, was maintained in DMEM supplemented with 10% FCS, sodium pyruvate, non-essential amino acids, L-glutamine and a 2-fold vitamin solution (Invitrogen, Karlsruhe Germany).

Antibodies and other reagents The human monoclonal antibody VFF18 against CD44v6 (14-mer: KEQWFGNRWHEGYR, SEQ ID NO:2) was obtained from Bender (Vienna, Austria). The pan-CD44 antibody IM7 was from BD Biosciences (San Diego, Calif.), the anti-Erk 1 (K-23) antibody was from Santa Cruz (Heidelberg, Germany). Antibodies directed against phospho-VEGFR-2 (Tyr1175) and phospho-Erk (Phospho-p44/42) were purchased from Cell Signaling Technology (Beverly, England). The antibody against VEGFR-2 was obtained from R&D Systems (Wiesbaden, Germany) or from Santa Cruz, Heidelberg (clone A-3). Secondary antibodies labeled with HRP were purchased from Dako (Hamburg, Germany). VEGF-A165 and VEGF-A121 were produced in Pichia pastoris. HGF was a generous gift of George Vande Woude (Van Andel Institute, Grand Rapids, USA). The v6 human peptide (14mer) and the control peptide have been described in Matzke et al., A 5-amino-acid peptide blocks Met and Ron dependent cell migration. *Cancer research* 65:6105-6110. The sequence of the v6 murine peptide was: QETWFQNGWQGKNP (SEQ ID NO: 3).

Constructs and protein production The VEGFR-2 expression plasmid pBE hVEGFR-2 was derived from the pEGFP-C1 vector from Clontech (Mountain View, Calif.) by introducing the sequence encoding the human VEGFR-2 with the PCR subcloning method to remove the GFP reading frame with the forward primer:

(SEQ ID NO: 4)
GCTCTTCGGGGAGCAGCGATGGAGAGCAAGGTGCTGCTG and the reverse primer:

(SEQ ID NO: 5)
GGAGGTTTTTTAAAGCAAGTAAAACCTTTATCACAGATCCTCTTCTGAG
AGAG

The constructs encoding the soluble wild type and mutant GST-CD44 cytoplasmic domain have been described and were obtained from C. Isacke (Breakthrough Breast Cancer Research Center, London, UK). The dominant negative ezrin (dn ezrin) expressing construct was a gift from M. Arpin (Institute Pasteur, Paris, France). The expression vectors for producing VEGF-A and the CD44v6 ectodomain (CD44v6ECD) in Pichia pastoris were generated using the pPICZαA vector system from Invitrogen (Carlsbad, Calif., USA). All expression vectors were made with the PCR subcloning technology and all recombinant proteins except for VEGF-A165 carried a hexa histidine tag at the amino terminus. Pichia pastoris strain X33 was transfected by electroporation and Zeocin resistant clones were picked and tested for transgene expression upon methanol induction. Secreted proteins were purified from the yeast culture supernatant by immobilized metal affinity chromatography (IMAC) and polished on Superdex 200 (GE Healthcare, München, Germany).

Exon-Specific RT-PCR The exon-specific RT-PCR was performed as described in König et al., 1996, Trans-acting factors regulate the expression of CD44 splice variants. *EMBO J.* 15:4030-4039, using the same human primers.

Transfection HEK293 cells were transiently transfected with Lipofectamine 2000 (Invitrogen, Karlsruhe, Germany) according to the manufacturer's protocol in a 6-well plate. Transfection of the BSp73AS cells and BSp73ASs6 cells was performed by electroporation. In brief, $3 \times 10^6$ cells were mixed with 5 µg of vector DNA on ice; the electroporation was performed in a 4-mm electroporation cuvette using a Gene Pulser (Bio-Rad, München, Germany) at 250 µF, 0.28 kV. Prewarmed medium containing serum was added and the cells were distributed in a 6-well plate. The cells were then grown for 24 h, serum starved for 24 h and used for the experiment.

Injections of tumor cells MDA-MB231 cells ($1 \times 10^6$ per animal) were harvested at subconfluency, washed with PBS and resuspended in 50 µl of PBS. The cells were implanted through a skin incision with an insulin syringe very slowly into the mammary fat pad of the fourth mammary complex of anesthetized female SCID mice (strain C.B-17/Ztm-scid). The incision was closed using an interrupted Vicryl suture for the skin (5/0, Ethicon, Norderstedt, Germany). The tumors were allowed to grow for one week, then the animals were divided in groups (6 to 7 animals per group) and treated with 20 µg of anti-mouse CD44v6 (clone 9A4), control IgG (NatuTec, Frankfurt, Germany), mouse v6 peptide or control peptide three times per week i.p. Tumor growth was monitored once per week using a caliper or via fpVCT imaging (see below). The animals were sacrificed 5 weeks after tumor cell implantation, the tumors were excised, measured, divided in halves and fixed in 4% formalin or zinc fixative (0.5 g/l calcium acetate, 5 g/l zinc acetate, 5 g/l zinc chloride in 0.1 M Tris pH 7.4) for 24 h for immunohistological analysis. L3.6pl human pancreatic cancer cells were injected orthotopically. Briefly, a small left abdominal flank incision was made and the spleen was exteriorized. $5 \times 10^5$ cells/40 µl Hanks buffered salt solution (Invitrogen, Karlsruhe Germany) were injected into the subcapsular region of the pancreas just beneath the spleen using a 30-gauge needle. A cotton swab was held for one minute on the side of injection to prevent leakage. An appearing fluid bleb was considered as sign for successful subcapsular intra-pancreatic injection. Seven days after implantation of the tumor cells, mice were randomly assigned to groups of 5 mice each: injection 3 times per week of (1) PBS, (2) of control peptide (20 µg/ml), (3) of CD44 v6 peptide (20 µg/ml). The animals were sacrificed 21 days after initiation of the treatment. The tumor volume was calculated as length×height×width divided by 2. Tissues were processed as described above. All animals were housed according to the German regulations for animal experimentation and all experiments were performed according to European and German statutory regulations. All mice were obtained from Harlan, Germany.

Flat-panel detector volume computed tomography (fpVCT) Imaging Mice were imaged with a none clinical volume computed tomography prototype flat-panel detector (GE Global Research, Niskayuna N.Y., US). In brief, the mice were anesthesized with 0.8-1% vaporized isoflurane and placed perpendicularly to the z-axis of the system. 30 seconds before scanning the iodine-containing contrast agent Isovist 300 (150 µl per mouse; Bayer-Schering, Berlin, Germany) was applied intraveneously. For better demonstration of small blood vessels, Isovist 300 was replaced by the blood pool agent eXia 160 (Binitio Biomedical Inc., Ottawa, Canada) that was used 90 seconds before scan at the day of dissection. All data sets were acquired with the same protocol: 500 views per rotation, 4 seconds rotation time, 360 used detector rows, tube voltage of 80 kVp and a current of 100 mA. A modified Feldkamp algorithm was used for image reconstruction resulting in isotropic high-resolution volume data sets (512× 512 matrix, with an isotropic voxel size of approximately 100 £gm). For tumor segmentation and volume estimation data sets were analyzed with voxtools 3.0.64 Advantage Workstation 4.2 (GE Healthcare, UK).

Activation of RTKs and Erk Serum starved cells (24 h) were induced with the growth factor HGF (20 ng/ml) at 37° C. for 5 min or with VEGF-A165 or VEGF-A121 (40 ng/ml) at 37° C. for 8 min. Where indicated, the cells were treated with blocking reagents prior to induction at 37° C. for 10 min (100 µg/ml anti-CD44v6, 100 ng/ml v6 peptide or 100 ng/ml control peptide, 0.5 µg/ml CD44v6ECD). Cells were washed with icecold PBS. To detect activated Erk, cells were lysed in boiling SDS-sample buffer containing 100 mM dithiothreitol (DTT) and subjected to Western blot analysis using antibodies against phosphorylated Erk. The Erk loading control was performed on the same blot stripped (62.5 mM Tris pH 6.8, 2% SDS, 0.8% DTT) and probed with the Erk antibody. To detect activated VEGFR-2, cells were lysed in reducing sample buffer and the blots of SDS-PAGE gels were probed with an antibody against phosphorylated VEGFR-2. Alternatively, lysates (20 mM Tris pH 7.4, 1 mM EDTA, 1 mM EGTA, 1 mM DTT, 25 mM NaCl, 1.5% Triton X-100, 10 mM NaF, 1 mM PMSF, 1 mM Na-orthovanadate, 1 mM aprotinin and leupeptin) were prepared. After centrifugation, the cleared lysates (12,000 rpm for 15 min) were incubated with VEGFR-2 antibody (clone A-3, Santa Cruz, Heidelberg, Germany) or a mouse IgG control (Santa Cruz, Heidelberg, Germany) at 4° C. overnight followed by incubation with Protein A/G agarose beads (Merck, Darmstadt, Germany) for 2 h at 4° C. The beads were washed three times, boiled in sample buffer and subjected to Western blot analysis using phosphospecific VEGFR-2 antibody. To obtain the loading control, the blots were stripped and reprobed with the VEGFR-2 antibody. Blots were stained using the enhanced chemiluminescence system (ECL, Thermo Fischer Scientific Inc., Waltham, Mass.). Bands in Western blot analysis were quantified with the program Image J.

Co-immunoprecipitation For co-immunoprecipitation, HUVECs ($1.5 \times 10^6$ in 10 cm plates) were induced by the respective ligands as described above. The cells were incubated in lysis buffer (25 mM Hepes pH 7.5, 100 mM NaCl, 10 mM $MgCl_2$, 1 mM EDTA, 10% Glycerol, 1% Igepal, 10 mM NaF, 1 mM PMSF, 1 mM Na-orthovanadate, 1 mM aprotinin and leupeptin) for 30 min on ice and then centrifuged for 20 min at 12000 rpm. For immunoprecipitation the cleared lysates were incubated with antibody against pan CD44 (IM7) at 4° C. overnight and then precipitated with protein A/G agarose beads (Merck, Darmstadt, Germany). The precipitates were washed three times in lysis buffer and subjected to Western blot analysis.

Scratch Assay HUVECs and HAOECs were seeded in 12-well plates at a concentration of $2.5 \times 10^5$ cells per well. After 24 hours a scratch was made into the confluent cell layer using a sterile pipette tip. The medium was changed and replaced by fresh medium or a medium containing 100 µg/ml anti-CD44v6, 100 ng/ml v6 peptide or 100 ng/ml control peptide. After 10 min at 37° C., induction with the growth factors (HGF (20 ng/ml), VEGF-A165 or VEGF-A121 (40 ng/ml)) was performed. Pictures of the cells were taken 24 hours after induction using a Canon Power Shot S620 digital camera. The computer program Image J was used for quantitative evaluation. The cell free area in the scratch was measured. The efficiency of the closure of the scratch is represented as percentage of cell free area.

Sprouting Assay Spheroids of HUVECs were generated in hanging drops. The cells were suspended in Endothelial Cell Growth Medium containing 0.25% (wt/vol) methylcellulose (Sigma, Hamburg, Germany) and incubated overnight (per spheroid: 750 cells in 25 µl). The spheroids were collected by gentle centrifugation (5 min, 800 rpm) and resuspended in Endothelial Cell Growth Medium containing 1 mg/ml rat tail collagen I (BD Biosciences, Bedford, Mass.) and 0.6% (wt/vol) methylcellulose. The spheroids/matrix mixture was distributed in 48-well plates (30 spheroids/well). After solidification of the collagen at 37° C., the spheroids/matrix mixture was overlayed with Endothelial Cell Growth Medium. Blocking reagents (100 µg/ml anti-CD44v6, 100 ng/ml v6 peptide or 100 ng/ml control peptide) were added and spheroids were induced by VEGFs (40 ng/ml). Pictures were taken 48 h later.

Tube formation assay 48-well plates were coated with growth factor reduced Matrigel (BD Biosciences, Bedford, Mass.) mixed with Endothelial Cell Growth Medium in a ratio 1:1. HUVECs were seeded on these Matrigel coated plates at a concentration of $2.5 \times 10^4$ cells per well. Blocking reagents (100 µg/ml anti-CD44v6, 100 ng/ml v6 peptide or 100 ng/ml control peptide) were added for 10 min at 37° C. followed by the induction with growth factors. Pictures were taken 24 h later. The quantification of tube formation was performed by counting the branching points or the total vessel length per field using the computer program Image J.

Collagen gel assay Angiogenic hyperplastic Langerhans islets obtained from Rip1 Tag2 mice at the age of 8 to 9 weeks were isolated by collagenase perfusion. HUVECs were mixed with blocking reagents and co-cultured with these islets in a three-dimensional collagen matrix in 24-well plates (per well: $4 \times 10^4$ cells in 350 µl collagen matrix, 5 angiogenic islets). Every third day new blocking reagents were added. After 5 to 7 days, the response of ECs to the angiogenic islets was determined. Approximately 60 islets per condition were analyzed.

Spheroid based in vivo angiogenesis assay This assay was performed as described previously (Alajati et al., 2008, Speroid-based engineering of a human vasculature in mice. Nat Methods 5:439-445). Spheroids of HUVECs were generated in hanging drops (25 Ml of growth medium containing 0.25% (wt/vol) methylcellulose (Sigma, Hamburg, Germany) containing 100 cells and incubated o/n. The spheroids were collected by gentle centrifugation (5 min, 800 rpm), washed with Endothelial Cell Growth Medium and mixed with 600 µl Matrigel (growth factor reduced; BD Biosciences, Heidelberg, Germany) and fibrinogen (final concentration 2 ml/ml; Calbiochem, Beeston, UK) containing the growth factors HGF or VEGF-A165 at a concentration of 500 ng/ml. 20 µg of CD44v6 antibody (VFF18) or peptide was added to the mixture followed by an addition of thrombin (0.4 U, Calbiochem, Beeston, UK). The mixture was injected subcutaneously on each side lateral to the abdominal midline region into 4-6 weeks old SCID mice. Every second day the blocking reagents (20 µg per mouse) were injected close to the Matrigel/fibrin plugs. Mice were sacrificed 21 days after implantation and plugs were retrieved and fixed over-night in 4% formaldehyde for immunohistological analysis.

Immunohistological analysis Following fixation, Matrigel/fibrin plugs or tumor tissues were processed and embedded in paraffin. 7 μm sections of paraffin blocks were deparaffinized and rehydrated. Matrigel/fibrin plug sections were stained with a mouse-anti-human CD34 antibody (clone QBEND/10, 20 μg/ml, 2 hours; Novocastra, Newcastle upon Tyne, UK) after blocking with 10% goat serum (Dako, Hamburg, Germany) for 60 min. The sections were then incubated with the goat-anti-mouse Alexa Fluor 488 (Invitrogen, Karlsruhe, Germany) for 45 min. Nuclei were stained with the Hoechst dye 33258 (Sigma Aldrich, Hamburg, Germany). Images of the complete Matrigel/fibrin area were taken using an OlympusIX50 inverted microscope. Fluorescent structures in the complete matrix area were counted and calculated as vessel number per $mm_2$. In the tumor sections, endogenous peroxidases were blocked with 3% $H_2O_2$ in PBS followed by incubation with avidin/biotin (Dako, Hamburg, Germany). Before incubation with the rat-anti-mouse CD31 antibody (0.5 μg/ml over night at 4° C.) unspecific binding was blocked with 10% rabbit serum (BD Biosciences, Heidelberg, Germany) for 60 min. Sections were then incubated with a biotinylated rabbit-anti-rat antibody (2 μg/ml, 45 min) followed by a streptavidin-peroxidase conjugate (Dako, Hamburg, Germany) treatment and developed with DAB substrate system (3,3'-diaminobenzidine, Biozol, Eching, Germany). With the computer program Image J all stained structures were analyzed for vessel number per $mm_2$ and average vessel size.

Quantification and statistical analysis All quantifications are given as mean±standard deviation (s.d.). Differences between the various conditions were analyzed by paired Student's test and $p<0.05$ was considered as statistically significant.

Example 1

CD44v6 Controls Activation of VEGFR-2 and Downstream Signaling

In a variety of cancer cell lines and primary cells, c-Met activation and signaling can be blocked by means of CD44v6 antibodies and peptides. In order to test whether a CD44 isoform could act as a co-receptor for c-Met also in ECs, it was first examined the expression profile of CD44 variants in HUVECs (human umbilical vein ECs) by exon-specific RT-PCR analysis (König et al., 1996, Trans-acting factors regulate the expression of CD44 splice variants. EMBO J. 15:4030-4039) (FIG. 1A). Several variant isoforms are indeed expressed. Interestingly, exon v6 seems to be expressed together with exon v7-10 (indicated by the ladder) and probably also alone (indicated by the lower band in the v6 lane). Note that v6 seems not to be co-expressed with exon v3 that appears as an independent isoform. c-Met can be activated in HUVECs and indeed, the HGF induced activation of Erk can be completely abrogated by a CD44v6 antibody and peptide (FIG. 1B).

This result suggests that in ECs, similarly to epithelial cells, CD44v6 isoforms act as co-receptors for c-Met. The effect of the CD44v6 antibody and peptide on the activation of VEGFR-2, the most prominent RTK involved in angiogenesis, was also tested. VEGFR-2 was activated with VEGF-A165, the predominant isoform of the VEGF family. Most interestingly, an antibody directed against exon v6 and a v6 specific peptide abrogated activation of VEGFR-2 and downstream Erk activation in HUVECs (FIGS. 1B and C). A control peptide had no effect.

To further confirm the dependency of VEGFR-2 and c-Met on CD44v6 in ECs, the effect of a soluble CD44v6 ectodomain (CD44v6ECD) on their activation was tested. The CD44v6ECD completely abrogated the activation of Erk induced by HGF and VEGF-A165 (FIG. 1D). In contrast, a CD44v6ECD mutated in the three amino acids instrumental for its co-receptor function for c-Met (Matzke et al., A 5-amino-acid peptide blocks Met and Ron dependent cell migration. *Cancer research* 65:6105-6110) did not have any effect (FIG. 1D). All CD44 proteins containing the exon v3 can be modified by heparan sulfate (HS). This modification seems to be required to bind growth factors such as FGF or HB-EGF. Binding of VEGF-165 to heparan sulfate proteoglycans and to HS modified CD44 isoforms has also been described. In order to address the requirement of HS residues for the activation of VEGFR-2, the HUVECs was activated with VEGF-A121 that lacks exons 6 and 7. Exon 7 accounts for binding to HS. VEGF-A121 was also able to activate VEGFR-2 and Erk in HUVECs (FIGS. 1D and 2A) and this activation was again completely blocked by the CD44v6ECD (FIG. 1D), a CD44v6 antibody and peptide (FIG. 2A).

Furthermore, in human kidney carcinoma cells (HEK293 cells) transfected with a VEGFR-2 expression vector, the CD44v6 peptide also blocked activation of VEGFR-2 induced by VEGF-A165 and VEGF-A121 (FIG. 2B). These results suggest that activation of VEGFR-2 occurs independently of HS modifications.

Moreover, the CD44v6 isoform playing a role in VEGFR-2 activation seems not to harbor the v3 sequence (exon v6 and exon v3 are not coexpressed on the same CD44 isoform as indicated by the RT-PCR analysis, FIG. 1A), the only sequence that can be modified by HS. To confirm that activation of VEGFR-2 was indeed independent of HS modification of CD44, it was tested whether a CD44 variant isoform containing exclusively the exon v6, as in the case of c-Met was sufficient for VEGFR-2 activation. VEGFR-2 expression vectors were transiently transfected either into rat BSp73AS pancreatic carcinoma cells that express only CD44s or into Bsp73AS cells stably transfected with CD44v6 (ASs6). Upon treatment with VEGF-A165 only the ASs6 cells were inducible (FIG. 2C).

Thus a CD44 variant isoform containing only variant exon v6 was sufficient to act as a VEGFR-2 co-receptor and again this co-receptor function does not require HS modification. The co-receptor function of CD44v6 for VEGFR-2 can be observed in several cell types such as HUVECs or HEK293 and ASs6 transfected with VEGFR-2.

The human cardiac microvascular ECs (HCMEC) and the human aortic ECs (HAOEC) are primary ECs where this collaboration between CD44v6 and c-Met or VEGFR-2 can also be demonstrated (FIGS. 3A and B). Indeed, in both cell types, VEGF-A165 activation of Erk is inhibited upon treatment of the cells with the CD44v6 peptide or the CD44v6 antibody (FIG. 3). A control peptide and control IgG have no effect. Cooperation amongst CD44 and VEGFR-2 implies that these proteins are in close proximity. Co-precipitation of endogenous CD44v6 and VEGFR-2 from HUVECs confirms this assumption (FIG. 3C).

Interestingly, the association between these two molecules appears to be constitutive and independent of addition of the ligand VEGF. This is in contrast to the CD44v6/c-Met association that is HGF-inducible. In the case of the c-Met receptor, the CD44 co-receptor associates with ERM proteins and the cytoskeleton in order to promote signaling. CD44v6, c-Met, HGF, ERM proteins and the cytoskeleton form a signalosome that allows activation of Ras by its GEF SOS.

To test if this mechanism also plays a role in the case of VEGFR-2, HEK293 cells were co-transfected with VEGFR-2 and a CD44 cytoplasmic domain-expressing vector to see if this domain would compete with the activity of endogenous CD44. This was indeed the case. In the presence of the CD44 cytoplasmic domain VEGFR-2 signaling to Erk was blocked without affecting VEGFR-2 phosphorylation itself (FIG. 4A). Expression of a CD44 cytoplasmic domain mutated in the ERM binding sequence had no effect on Erk and VEGFR-2 activation (FIG. 4A). From these experiments it can be concluded that the activation of VEGFR-2 is independent of the cytoplasmic domain of CD44, whereas signal transduction requires this domain and the binding of ERM proteins.

To directly address the involvement of ERM proteins HEK293 cells were transfected with VEGFR-2 together with an ezrin dominant negative (dn) construct lacking the actin binding domain (FIG. 4B). This truncated version of ezrin also inhibited VEGF-A165 and VEGF-A121 signaling to Erk, again indicating that the binding of ERM proteins to the cytoskeleton is required for signaling from VEGFR-2.

In conclusion, CD44v6 is a co-receptor for VEGFR-2 in ECs. The CD44v6 antibody, peptide and a CD44v6ECD block VEGFR-2 activation. The two molecules form a constitutive complex as demonstrated by coimmunoprecipitation experiments. In addition, the cytoplasmic domain of CD44v6 recruits ERM proteins and the cytoskeleton to promote signaling.

Example 2

A CD44v6 Peptide and Antibody Block the Response of ECs to VEGF

The angiogenic process comprises several steps ultimately leading to the formation of new capillaries. First the basal lamina surrounding blood vessels is locally destroyed so that ECs can invade the stroma. The ECs proliferate, migrate and finally adhere to each other to form new tubules. Several of these steps can be mimicked in vitro. In a scratch assay, migration of ECs can be measured. HGF and VEGF-A induced migration of HAOECs leading to closure of a scratch in a confluent monolayer (FIG. 5). In the presence of the v6 peptide or antibody, this process was strongly inhibited. Measurement of proliferation using a 3H-Thymidine incorporation assay revealed that the cells are not proliferating during the time of the observation (not shown). The same assay was performed using HUVECs leading to similar results (FIG. 5).

ECs have the property to form spheroids when grown in methylcellulose. Spheroids from HUVECs, transferred to collagen in the presence of VEGFA165 and VEGF-A121, sprout (FIG. 6A). Sprouting was strongly inhibited by the CD44v6 peptide but not by a control peptide (FIG. 6A, quantification in the graph). Finally a tubular network formation assay was used to test the role of CD44 in the establishment of new blood vessels. HUVECs were grown on growth factor-reduced Matrigel and treated with HGF, VEGF-A165 or VEGF-A121 in the presence or absence of a v6 peptide and antibody.

In the absence of growth factors, a preliminary network can be observed (FIG. 6B) likely due to traces of growth factors in the Matrigel. Induction with the different growth factors increased the density of the network. Treatment with the CD44v6 peptide or antibody interfered with the formation of the network while a control peptide had no effect. Quantification of this assay revealed that the number of branching points was drastically reduced to 50% for HGF and to 30% for VEGF-A165 and VEGF-A121 (FIG. 6B). The length of the vessels was also decreased to 60% for HGF and to approximately 45% for VEGF-A165 and VEGF-A121.

In conclusion, various assays such as scratch closure, spheroid sprouting and tubular network formation demonstrate that the response of ECs to HGF, VEGF-A165 and VEGF-A121 requires CD44v6.

Example 3

Angiogenic Response Induced by Hyperplastic Langerhans Islets Isolated from the Rip1Tag2 Mice is Dependent on CD44v6

So far several growth factors were tested separately and looked at their effect using in vitro assays. An ex-vivo experiment was also performed where hyperplastic Langerhans islets were isolated from Rip1Tag2 mice and incubated with HUVECs (FIG. 7A). The Rip1Tag2 mouse model is a well defined model of insulinoma. These transgenic animals express the SV40 large T antigen under the control of the rat insulin promoter resulting in expression of T antigen exclusively in the Langerhans islets of the pancreas. During multistage tumor development hyperplastic islets progressively induce tumor angiogenesis by the activation of a variety of angiogenic factors.

Langerhans islets were isolated at a stage where the majority are angiogenic (8-9 weeks old mice) and incubated them with HUVECs in the presence of the CD44v6 antibody or peptide. Release of angiogenic factors from the Langerhans islets promotes growth of HUVECs towards them. About 60% of the islets were angiogenic. In the presence of the CD44v6 antibody or peptide the angiogenic activity of Langerhans islets was blocked (FIG. 7A). Thus even when several growth factors mediate the angiogenic response, blocking of the co-receptor function of CD44v6 reduced this response.

Example 4

In vivo Development of Blood Vessels from Grafted EC Spheroids is Impaired Upon Treatment with CD44v6 Blocking Reagents A human vasculature can be engineered from human EC spheroids embedded together with growth factors in Matrigel/fibrin upon grafting into the flank of SCID mice. This assay was used to test whether CD44v6 is involved in the development of this vasculature. HUVEC spheroids embedded in Matrigel/fibrin containing either HGF or VEGF-A165 together with the CD44v6 peptide or antibody (or a control peptide or IgG) were subcutaneously injected into the flank of SCID mice. The formation of the human vascular network was determined three weeks later by staining of the Matrigel/fibrin plugs with human CD34 antibodies. Both, HGF and VEGF, induced vessel formation (FIG. 7B) that was not detectable in the absence of either growth factor (not shown). A CD44v6 peptide and a v6 specific antibody significantly reduced the angiogenic response to more than 50% (FIG. 7B). Thus, also in this assay the angiogenic response is dependent on CD44v6. Furthermore, these results confirm that HGF can act as an angiogenic factor.

Example 5

Vascularization of a Mammary and a Pancreatic Tumor Requires CD44v6

To prove whether tumor induced angiogenesis can be repressed by a CD44v6 peptide and antibody it was made use of human mammary (MDA-MB231) and human pancreatic carcinoma cells (L3.6pl). Both cells have already been used to study angiogenesis in orthotopic human tumors in mice (MDAMB231:, L3.6pl:). MDA-MB231 cells were implanted into the mammary fat pad of SCID mice whereas L3.6pl cells were injected into the tail of the pancreas of SCID mice. One week later a CD44v6 peptide or antibody (or a control peptide or control IgG) was administered intraperitoneally three times per week for four weeks in the case of MDA-MB231 tumors or for three weeks in the case of L3.6pl tumors.

So far a CD44v6 human peptide and a human antibody were used to target human ECs. In the tumor models, however, a mouse specific antibody and peptide were used. CD44v6 peptides are species specific and do not crossreact. In particular, the CD44v6 peptide and the CD44v6 antibody used in the orthotopic tumor models did not interfere with CD44 functions on tumors cells (human). Thus they targeted only angiogenesis of host ECs. In the case of MDA-MB231 tumors, two groups of animals either treated with the CD44v6 antibody or a control IgG were examined using flat-panel detector Volume Computed Tomography (fpVCT) to follow tumor growth and tumor vascularization over time. At the end of the experiment tumors were isolated from all animals, sections were made and stained with a CD31 antibody. The vessel density and the vessel length were estimated from the stained sections. For MDA-MB231 tumors, tumor growth was not influenced by the murine CD44v6 peptide or antibody (not shown). Also the average vessel size was not influenced by the CD44v6 tools (Table 1). In contrast the microvessel density was significantly decreased, from 240 to 183 per mm$^2$ by the CD44v6 peptide and 247 to 220 mm$^2$ by the antibody (Table 1). Similarly, a decrease in tumorsurrounding and invading small vessels was observed by fpVCT in mice treated with the antibody (FIG. 8A). This decrease was already visible three weeks after implantation and could be followed to the end of the experiment after 5 weeks (FIG. 8A).

In contrast, a drastic inhibitory effect of the CD44v6 peptide was observed already on the growth of the human pancreatic tumors established from L3.6pl cells: the tumor size was reduced to ten percent (FIG. 8B). Furthermore, as well vessel density and the vessel size were decreased by more than 60 percent upon treatment with the CD44v6 peptide (FIG. 8B). These data suggest that the growth of this pancreatic tumor is particularly dependent on the establishment of a blood vasculature. In conclusion it has been shown that the CD44v6 peptide and antibody not only block the activation and signaling of VEGFR-2 on several ECs and thereby interfere with tubular outgrowth and EC migration in a variety of test systems but that they also inhibit tumor induced blood vessel formation in vivo.

TABLE 1

Inhibition of tumor-induced blood vessels by a CD44v6 peptide and antibody

|  | IgG | αCD44v6 | ctrl peptide | v6 peptide |
|---|---|---|---|---|
| average vessel number (per mm$^2$) | 247.6 | 220.1 | 240.3 | 183.7 |
| stdev | 22.5 | 20.1 | 24.4 | 31.7 |
| significance |  | 0.025 |  | 0.007 |
| average vessel size (μm$^2$) | 192.9 | 203.9 | 207.8 | 211.4 |
| stdev | 11.5 | 33.7 | 28.1 | 31.7 |

Injection of MDA-MB231 cells into SCID mice and subsequent treatments were performed as described in FIG. 7A. Tumor sections were stained with CD31 specific antibodies and the blood vessel number and size were counted. The numbers reflect the counts of five animals each.

In the above experiments it has been shown that the activation of c-Met and VEGFR-2 by their respective ligands in ECs is strictly dependent on a CD44 isoform containing the variant exon v6. In HUVECs, a CD44v6 specific antibody, a v6 peptide and a CD44v6ECD abrogate both c-Met and VEGFR-2 activation and subsequent induction of EC migration, spheroid sprouting and tubule formation. Coimmunoprecipitation studies show that VEGFR-2 and CD44v6 form a complex and seem to be constitutively associated with each other. The dependency of VEGFR-2 towards CD44v6 is not only true in HUVECs but also in HAOECs and HCMECs and can be simulated in other cells (HEK293 cells and ASs6 cells) transfected to express VEGFR-2.

Since HGF and c-Met are also important in angiogenesis, it was examined whether they cooperate with CD44v6 isoforms also in ECs. A CD44v6 specific peptide as well as a CD44v6 antibody can indeed block c-Met activation on ECs and HGF induced migration and tubular vessel formation by ECs is impaired. Most interestingly, this peptide and antibody also blocked VEGF induced VEGFR-2 activation. In addition, ERM proteins that associate with CD44 regulate signaling from VEGFR-2. Therefore, the mechanism of action of CD44 seems very similar for both c-Met and VEGFR-2 activation. Indeed, CD44v6 controls physiological changes, including the formation of blood vessels in vitro and even in tumors.

It has been demonstrated above that activation of VEGFR-2 can be induced also by the non heparin-binding VEGF-A121, and that this activation is also dependent on CD44 exon v6. Furthermore, although ECs express CD44 exon v3 and exon v6, these exons seem not to be present on the same protein as deduced from RT-PCR analysis. Finally, activation of VEGFR-2 was observed in BSp73ASs6 cells that express only CD44v6 and CD44s but not the CD44v3 heparan sulfated form. These results indicate that activation of VEGFR-2 per se may not rely on HS. It seems, however, that binding to HS is required for a full-blown angiogenic response. A cooperation between VEGFR-2, VEGF, neuropilin and CD44v6 is likely involved in a full-blown angiogenic response.

The co-receptor function of CD44v6 for VEGFR-2 is highly relevant in tumor angiogenesis as shown by the effect of the CD44v6 peptide and the CD44v6 antibody on two different orthotopic tumor models. Blocking CD44v6 in tumors originating from human mammary carcinoma MBA-MD231 cells has a significant effect on the microvessel density whereas the average vessel size and the tumor growth rate are not affected. In the human pancreatic tumors originating from the L3.6pl cells, tumor size as well as microvessel density and average vessel size are drastically decreased after treatment with the CD44v6 peptide. The different responses of these two tumor systems might be due to the intrinsic properties of the cancer cells. One possibility is that the angiogenic factors produced in both cases are different. Since CD44v6 can act as a co-receptor for c-Met, VEGFR-2, Trk and specific members of the EGFR family of RTKs but not for PDGFRs or FGFRs, the effect of the blocking reagents might differ according to which angiogenic growth factors are produced. The findings here that CD44 isoforms are relevant for angiogenesis add a new dimension to the role of CD44 in tumorigenesis.

The invention claimed is:

1. A method for treating an ophthalmic disease associated with overexpression of Vascular Endothelial Growth Factor Receptor-2 (VEGFR-2) in an individual, the method comprising administering to an individual an effective amount of a peptide compound comprising amino acids 7 to 11 of SEQ ID NO:2, or a pharmaceutically acceptable salt thereof.

2. The method according to claim 1, wherein the ophthalmic disease is associated with hyperproliferation of endothelial cells.

3. The method according to claim 1, wherein the ophthalmic disease is macular degeneration or diabetic retinopathy.

4. The method according to claim 1, wherein the individual is a mammal.

5. The method according to claim 1, wherein the peptide compound comprises amino acids 7 to 11 of SEQ ID NO: 2 and the individual is a human.

6. The method according to claim 1, wherein the peptide compound is a cyclopeptide or a pharmaceutically acceptable salt thereof.

* * * * *

SEQUENCE LISTING

<160> NUMBER OF SEQ ID NOS: 5

<210> SEQ ID NO 1
<211> LENGTH: 14
<212> TYPE: PRT
<213> ORGANISM: Rattus norvegicus

<400> SEQUENCE: 1

Lys Glu Lys Trp Phe Glu Asn Glu Trp Gln Gly Lys Asn Pro
1               5                   10

<210> SEQ ID NO 2
<211> LENGTH: 14
<212> TYPE: PRT
<213> ORGANISM: Homo sapiens

<400> SEQUENCE: 2

Lys Glu Gln Trp Phe Gly Asn Arg Trp His Glu Gly Tyr Arg
1               5                   10

<210> SEQ ID NO 3
<211> LENGTH: 14
<212> TYPE: PRT
<213> ORGANISM: Mus musculus

<400> SEQUENCE: 3

Gln Glu Thr Trp Phe Gln Asn Gly Trp Gln Gly Lys Asn Pro
1               5                   10

<210> SEQ ID NO 4
<211> LENGTH: 39
<212> TYPE: DNA
<213> ORGANISM: Artificial Sequence
<220> FEATURE:
<223> OTHER INFORMATION: Synthetic

<400> SEQUENCE: 4
gctcttcggg gagcagcgat ggagagcaag gtgctgctg                              39

<210> SEQ ID NO 5
<211> LENGTH: 53
<212> TYPE: DNA
<213> ORGANISM: Artificial Sequence
<220> FEATURE:
<223> OTHER INFORMATION: Synthetic

<400> SEQUENCE: 5
ggaggttttt taaagcaagt aaaaccttta tcacagatcc tcttctgaga gag             53